United States Patent [19]

White, Jr.

[11] 4,151,168
[45] Apr. 24, 1979

[54] 5-PHENYL-2-OXAZOLE CARBOXIMIDAMIDES AS ANTIDEPRESSANTS

[75] Inventor: Ralph L. White, Jr., Norwich, N.Y.

[73] Assignee: Morton-Norwich Products, Inc., Norwich, N.Y.

[21] Appl. No.: 881,827

[22] Filed: Feb. 27, 1978

[51] Int. Cl.² .......................................... C07D 263/34
[52] U.S. Cl. ................................ 260/307 R; 424/272
[58] Field of Search .................................. 260/307 R

[56] References Cited

U.S. PATENT DOCUMENTS 3,325,506  6/1967  Jones et al. .......................... 260/302

Primary Examiner—Raymond V. Rush
Attorney, Agent, or Firm—Anthony J. Franze

[57] ABSTRACT

A series of 5-phenyl-2-oxazole carboximidamides are useful as antidepressants.

4 Claims, No Drawings

5-PHENYL-2-OXAZOLE CARBOXIMIDAMIDES AS ANTIDEPRESSANTS

This invention is concerned with chemical compounds and more particularly with a series of 5-phenyl-2-oxazole carboximidamides of the formula:

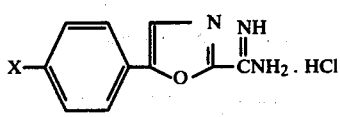

wherein X is hydrogen, nitro or chloro. The members of this series are useful as antidepressants.

Their useful antidepressant activity is exhibited in warm blooded animals under the standard ptosis-antitetrabenazine test. Thus, when administered perorally in suspension (0.5 percent aqueous methyl cellulose) or aqueous solution in a dose of about 50 mg/kg to mice shortly prior to intraperitoneal administration of from 1-10 mg/kg of tetrabenazine, ptosis induced by tetrabenazine is curtailed to the extent of from 50-90 percent.

The compounds of this invention are readily composed in a variety of pharmaceutical dosage forms such as tablets, elixirs, suspensions, capsules and the like using commonly employed excipients and adjuvants with which there is no incompatibility.

The method which is currently preferred for the making of the compounds of this invention is illustrated in the following examples.

EXAMPLE I

5-Phenyl-2-oxazolecarboximidamide

A. 5-Phenyl-2-oxazolecarboxaldehyde Oxime

Hydroxylamine hydrochloride (54 g, 0.78 mole) and 1-[[[5-phenyl-2-oxazolyl]methylene]amino]-2,4-imidazolidinedione (105 g, 0.39 mole) were refluxed with stirring in a solution of water (100 ml) and glacial acetic acid (1.0 l.) for five hrs. An additional 54 g of hydroxylamine hydrochloride was added while the mixture was refluxed another five hrs. The hot solution was treated with Darco, filtered and poured into water (5.0 l.). The solid was again refluxed in a mixture of hydroxylamine hydrochloride (50 g), acetic anhydride (800 ml) and water (80 ml) for four hrs. The solution was cooled, poured into water (3.0 l.) and the resulting solid was collected and dried (48 g, 65%). Recrystallization of a sample from acetonitrile gave product of analytical purity, m.p. 208°-210°.

B. 5-Phenyl-2-oxazolecarboximidamide

A (32 g, 0.17 mole) and sodium acetate (anhyd., 14 g, 0.17 mole) were refluxed in acetic anhydride (300 ml) for four hrs. The mixture was cooled, poured into water (2.0 l.) and allowed to stir overnight. Filtration yielded brown solid. The dried solid was dissolved in hot toluene and then cooled to yield a crystalline impurity. The filtrate was concentrated under reduced pressure to a solid which was recrystallized from acetonitrile to give 18 g (62%) of the nitrile, m.p. 73°-75°.

The nitrile (15 g, 0.090 mole) was dissolved in methanol (250 ml) and sodium methoxide (4.8 g, 0.089 mole) was then added. The solution was stirred for six hrs. and then concentrated under reduced pressure to a solid. Water (200 ml) was added to the solid residue and the imidate (18 g, 99%) was collected and dried.

The imidate (18 g, 0.089 mole) and anhydrous ammonium chloride (5.0 g, 0.093 mole) were slowly heated to reflux over an hour in methanol (150 ml) and the solution was allowed to reflux for three hours. The mixture was concentrated under reduced pressure to a solid. Recrystallization of the solid from ethanol yielded 14 g (70%, 43% overall) in two crops, m.p. 286°-87°.

Anal. Calcd. for $C_{10}H_9N_3O \cdot HCl$: C, 53.70; H, 4.51; N, 18.79. Found: C, 53.86; H, 4.54; N, 18.93.

EXAMPLE II

5(4-Nitrophenyl)-2-oxazolecarboximidamide Hydrochloride

A mixture of 1-[[[5-(4-nitrophenyl)-2-oxazoyl]methylene]amino]-2,4-imidazolidinedione (28 g, 10.089 mole), hydroxylamine hydrochloride (28 g.), acetic acid (300 ml) and water (30 ml) was stirred and refluxed for 1.5 hrs. The mixture was allowed to cool to room temperature and was poured into ice-water (3 l). The solid was collected by filtration and allowed to air-dry to give 17 g of the oxime.

A stirred mixture of the above oxime (17 g, 0.072 mole), sodium acetate (12 g, 0.15 mole) and acetic anhydride (80 ml) was slowly heated to reflux over a period of 2 hrs. The dark solution was poured into ice-water (4 l) to give a precipitate. The mixture was allowed to stand overnight, and the solid was collected by filtration to give 16 g of the nitrile.

A stirred mixture of the above nitrile (16 g, 0.066 mole) in methanol (500 ml) was cooled on an ice bath before sodium methoxide (346 g, 0.066 mole) was added. The mixture was stirred for 1 hr. on the ice bath. The mixture was filtered and washed with water to give 20 g of the imidate.

A mixture of the above imidate (20 g, 0.092 mole), ammonium chloride (4.5 g, 0.092 mole) and methanol (600 ml) was stirred at room temperature overnight. The stirred mixture was refluxed for 12 hrs. More ammonium chloride (2.3 g, 0.05 mole) was added to the reaction and the mixture was refluxed for 20 hrs. The mixture was filtered to give starting imidate (9 g). The filtrate was evaporated under reduced pressure to give the amidine (15 g).

A mixture of the recovered imidate (9 g, 0.038 mole), ammonium chloride (2.1 g, 0.038 mole) and methanol (500 ml) was stirred and refluxed for 48 hrs. More ammonium chloride (1.0 g) was added to the reaction and the mixture was stirred and refluxed for 70 hrs. The mixture was filtered to give imidate (4 g). The filtrate was evaporated under reduced pressure to give the amidine 8.6 g. The two crops of amidine were combined and washed with isopropanol to give 21 g (88%). A sample was recrystallized from methanol (75 ml) to give analytical purity, m.p. >300°.

Anal. Calcd. for $C_{10}H_8N_4O_3 \cdot HCl$: C, 44.70; H, 3.67; N, 20.86. Found: C, 45.04; H, 3.29; N, 20.62.

EXAMPLE III 5-(4-Chlorophenyl)-2-oxazolecarboximidamide Hydrochloride

1-[[5-(p-chlorophenyl)-2-oxazoyl methylene]amino]-2,4-imidazolidinedione (76.6 g, 0.25 mole) was refluxed with hydroxylamine hydrochloride (76.7 g, 1.10 mole) in a solution of acetic acid (660 ml) and water (60 ml) for 3 hrs. The solution was cooled and filtration yielded a solid. Recrystallization from acetic acid gave the crude oxime, 63.7 g, 0.29 mole (yield >100%).

The oxime (6.18 g, 0.28 mole) was refluxed with phosphorus oxychloride (300 ml). A strong exothermic reaction occurred within 30 minutes and heat was removed. Heating at reflux temperature was resumed for 1 hr., and the solution was cooled and poured into stirred ice-water (6 l). After 20 hrs., crude solid was collected, stirred in hot toluene (650 ml) and cooled to room temperature. Filtration allowed removal of an insoluble solid, and the filtrate was stripped of solvent to a solid. Recrystallization of the crude solid from hexane gave 17.7 g (0.08 mole, 31%) of nitrile, m.p. 124°–131°.

Anal. Calcd. for $C_{10}H_5ClN_2O$: C, 58.70; H, 2.46; N, 13.69. Found: C, 58.82; H, 2,43; N, 13.63.

5-(4-Chlorophenyl)-2-oxazolecarbonitrile (17.7 g, 0.086 mole) was dissolved in methyl alcohol (500 ml) and stirred with sodium methoxide (0.5 g. 0.009 mole) for 20 hrs. The mixture was filtered, solid collected and filtrate concentrated to a solid. The two solids were combined and washed with water, collected and air-dried to give 19.7 g of crude imidate intermediate.

The above intermediate (19.7 g, 0.083 mole) was stirred with ammonium chloride (4.5 g, 0.083 mole) in methanol (500 ml) for 6 hrs., then refluxed for 4 hrs., filtered hot, and stripped of solvent to a solid. Recrystallization from ethanol gave 13.3 g (0.048 mole, 56%; overall yield, 17.4%) m.p. 275°–276° C.

Anal. Calcd. for $C_{10}H_8CiN_3O\cdot HCl$: C, 46.53; H, 3,51; N, 16.28. Found: C, 46.17; H, 3.57; N, 16.02.

What is claimed is:

1. A compound of the formula:

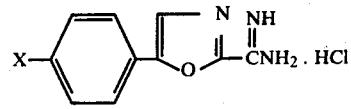

wherein X is hydrogen, nitro or chloro.

2. The compound 5-phenyl-2-oxazolecarboximidamide hydrochloride.

3. The compound 5-(4-nitrophenyl)-2-oxazolecarboximidamide hydrochloride.

4. The compound 5-(4-chlorophenyl)-2-oxazolecarboximidamide hydrochloride.

* * * * *